United States Patent
He

(10) Patent No.: US 9,025,149 B2
(45) Date of Patent: May 5, 2015

(54) SCREENING METHOD OF A PHOSPHOR-BASED OPTICAL FILM USED IN A BACKLIGHT MODULE AND BACKLIGHT MODULE THEREOF

(71) Applicant: Shenzhen China Star Optoelectronics Technology Co., Ltd., Shenzhen, Guangdong (CN)

(72) Inventor: Hu He, Shenzhen (CN)

(73) Assignee: Shenzhen China Star Optoelectronics Technology Co., Ltd., Shenzhen, Guangdong (CN)

( * ) Notice: Subject to any disclaimer, the term of this patent is extended or adjusted under 35 U.S.C. 154(b) by 39 days.

(21) Appl. No.: 14/116,762

(22) PCT Filed: Sep. 4, 2013

(86) PCT No.: PCT/CN2013/082938
§ 371 (c)(1),
(2) Date: Nov. 9, 2013

(87) PCT Pub. No.: WO2015/027528
PCT Pub. Date: Mar. 5, 2015

(65) Prior Publication Data
US 2015/0062583 A1     Mar. 5, 2015

(30) Foreign Application Priority Data
Sep. 2, 2013    (CN) .......................... 2013 1 0392976

(51) Int. Cl.
*G01J 3/46*     (2006.01)
*G01N 21/25*    (2006.01)
*F21V 8/00*     (2006.01)

(52) U.S. Cl.
CPC .............. *G01N 21/25* (2013.01); *G02B 6/0035* (2013.01)

(58) Field of Classification Search
USPC ................................................... 356/402–425
See application file for complete search history.

(56) References Cited

U.S. PATENT DOCUMENTS

2011/0294240 A1*   12/2011   Kim ............................... 438/16

FOREIGN PATENT DOCUMENTS

| CN | 102759050 A | 10/2012 |
| CN | 102929035 A | 2/2013 |

* cited by examiner

*Primary Examiner* — Abdullahi Nur
(74) *Attorney, Agent, or Firm* — Andrew C. Cheng

(57) ABSTRACT

A screening method of a phosphor-based optical film used in a backlight module and a backlight module are proposed. The screening method includes steps of: a) dividing an internal surface of the backlight module without a phosphor-based optical film into multiple measurement zones, and gaining a transmittance spectrum of each of the measurement zones; b) gaining a chromatic value of each of the measurement zones matching the phosphor-based optical film; c) checking the chromatic values gained in b) to be within a range of standard chroma; the process of screening being finished if all of the chromatic values are in the range; matching at least one measurement zone with a new phosphor-based optical film if the chromatic value of the at least one of the measurement zones is not within the range, and returning to b). The present backlight module has higher saturation and penetration and better color uniformity.

16 Claims, 3 Drawing Sheets

SCREENING METHOD OF A PHOSPHOR-BASED OPTICAL FILM USED IN A BACKLIGHT MODULE AND BACKLIGHT MODULE THEREOF

BACKGROUND OF THE INVENTION

1. Field of the Invention

The present invention relates to the field of liquid crystal display (LCD), and more particularly, to a screening method of a phosphor-based optical film used in a backlight module and a backlight module thereof.

2. Description of the Prior Art

A liquid crystal display (LCD) has been broadly applied for advantages over slimness, power-saving, and low radiation. The LCD mainly comprises an LCD panel and a backlight module. The backlight module is set up in opposite to the LCD panel and provides a display light source to it so that the LCD panel displays images by the light from the backlight module.

Conventionally, there are two types of the backlight module, direct and side-in backlight module. No matter of direct or side-in backlight module, however, a light source as a core decides a display effect of the backlight module, such as brightness, chroma and color saturation of the backlight module. The brightness of the backlight module is adjustable by luminous flux, amount, driving methods of the light source and a framework of optical films in the backlight module. The chroma of the backlight module is suited to a standard by a spectrum of the light source, a transmittance spectrum of optical material and a color filter spectrum. The color saturation of the backlight module, as an additional norm, is mainly used for distinguishing a high-class type (i.e. high-class LCD) and a low-class type (i.e. low-class LCD). A norm of the color saturation of the backlight module in a common low-class type is around 62% to 70%. On the other hand, a norm of the color saturation of the backlight module in a high-class type is over 75%. In addition, uniformity of chromaticity on a backlight module side optimizes visual perception of an LCD. For instance, chromatism of the backlight module inside in a low-class type is limited below 0.010.

As FIG. 1 shows, the side-in backlight module comprises a light guide plate (LGP) 10, a light source 20 close to a light-in side of the LGP 10 and a phosphor powder optical film 30 on a light-out side of the LGP 10. The light source 20 adopts blue light-emitting diodes, and the phosphor powder optical film 30 transforms part of blue light from the light source 20 into red and green light, and then the rest of blue light and the transformed red and green light are mixed to get white light as a backlight source of a backlight module. Compared with the white LED as a light source of the backlight module, the backlight module in FIG. 1 optimizes to fit for a color filter in an LCD to achieve better color saturation and transmittance. A material of the LGP (polymethylmethacrylate, MS, etc) and existence of mesh points in the LGP, however, result in that the LGP observes more blue light so that chroma of the LGP in a direction far away the light source increases gradually, and therefore have a strong impact on uniformity of chromaticity of the backlight module inside.

SUMMARY OF THE INVENTION

According to the present invention, a screening method of a phosphor-based optical film used in a backlight module, comprises steps of: a) dividing an internal surface of the backlight module without the phosphor-based optical film into a plurality of measurement zones, and gaining a transmittance spectrum of each of the plurality of measurement zones; b) gaining a chromatic value of each of the plurality of measurement zones after each of the plurality of measurement zones matches the phosphor-based optical film; c) checking the chromatic value of each of the plurality of measurement zones gained in b) to be within a range of standard chroma; the process of screening of the phosphor-based optical film used in the backlight module being finished if the chromatic value of each of the plurality of measurement zones matching the phosphor-based optical film is in the range of standard chroma; matching at least one measurement zone with a new phosphor-based optical film if the chromatic value of the at least one of the measurement zones matching the phosphor-based optical film is not within the range of standard chroma, and returning to Step b).

Further, Step b) further comprises steps of: Step b1) gaining the transmittance spectrum of the phosphor-based optical film matching each of the plurality of measurement zones; Step b2) gaining the transmittance spectrum of the phosphor-based optical film after each of the plurality of measurement zones matches the phosphor-based optical film; Step b3) gaining a chromatic value of each of the plurality of measurement zones after each of the plurality of measurement zones matches the phosphor-based optical film based on the transmittance spectrum gained in Step b2).

Further, the phosphor-based optical film matching each of the plurality of measurement zones comprises different producing parameters.

Further, the phosphor-based optical film is a quantum dot film.

According to the present invention, a screening method of a phosphor-based optical film used in a backlight module, comprises steps of: a) dividing an internal surface of the backlight module without the phosphor-based optical film into a plurality of measurement zones, and gaining a transmittance spectrum of each of the plurality of measurement zones; b) gaining the transmittance spectrum of an n phosphor-based optical film, and n being a positive integer; c) gaining the transmittance spectrum of an m measurement zone after the m measurement zone matches the n phosphor-based optical film, and m being a positive integer; d) gaining a chromatic value of the m measurement zone after each of the m measurement zone matches the n phosphor-based optical film based on the transmittance spectrum gained in Step c); e) checking the chromatic value of the m measurement zone after the m measurement zone matches the n phosphor-based optical film gained in Step d) to be within a range of standard chroma; if the chromatic value of the m measurement zone after the m measurement zone matches the n phosphor-based optical film is not in the range of standard chroma, returning to Step b) where n is set as n+1 (n=n+1); if the chromatic value of the m measurement zone after the m measurement zone matches the n phosphor-based optical film is within the range of standard chroma, returning to Step c) where m is set as m+1 (m=m+1).

Further, the phosphor-based optical film is a quantum dot film.

Further, each of the phosphor-based optical films comprises different producing parameters.

Further, each of the phosphor-based optical films comprises different producing parameters.

According to the present invention, a backlight module comprises a light source and a light guide plate (LGP). The LGP comprises a light input surface and a light output surface, and the light source being disposed near the light input surface. The backlight module further comprises a phosphor-based optical film which is screened according to the screening method as mentioned above. The phosphor-based optical film is disposed on the light output surface.

Further, the phosphor-based optical film is a quantum dot film.

Further, the phosphor-based optical film is disposed on the light output surface by means of printing or spray coating.

A phosphor-based optical film can be used as backlight of a backlight module, for the phosphor-based optical film eventually converts light produced by a light source into white light. Producing parameters of the phosphor-based optical film vary with which part of a measurement zone of the backlight module matching the phosphor-based optical film. Different phosphor-based optical films have different producing parameters. So the phosphor-based optical film highly matches the backlight module. The backlight module of the present invention has higher saturation and penetration and better color uniformity.

DETAILED DESCRIPTION OF THE PREFERRED EMBODIMENTS

The accompanying drawings are included to provide a further understanding of the invention, and are incorporated in and constitute a part of this specification. The drawings illustrate embodiments of the invention and, together with the description, serve to explain the principles of the invention.

Embodiment 1

Figure 1:
FIG. 1 shows a conventional backlight module capable of upgrading color saturation.
Figure 2:
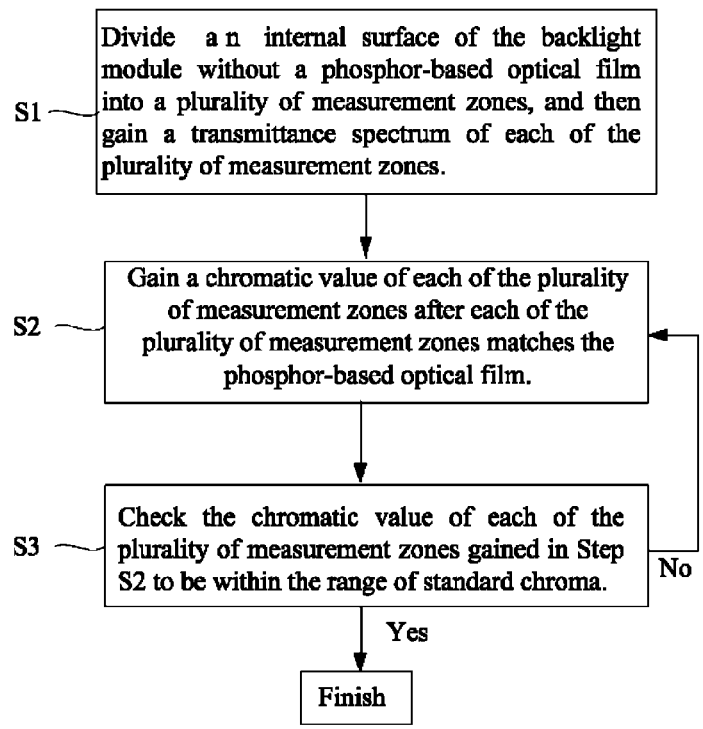
FIG. 2 is a flow chart showing a screening method of a phosphor-based optical film used in a backlight module according to a first embodiment of the present invention.

FIG. 2 is a flow chart showing a screening method of a phosphor-based optical film used in a backlight module according to a first embodiment of the present invention.

Figure 3:
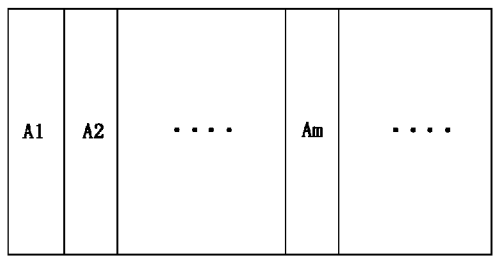
FIG. 3 shows an example of dividing measurement zones.

As shown in FIG. 2, the screening method of the phosphor-based optical film comprises following steps:

Step S1: Divide the internal surface of the backlight module without a phosphor-based optical film into a plurality of measurement zones, and then gain a transmittance spectrum of each of the plurality of measurement zones. The plurality of measurement zones can be distributed from one side of the backlight module to the farthest side in this step. For example, a first measurement zone A1, a second measurement zone A2, . . . , an m measurement zone Am are distributed in order from one side of the backlight module to the farthest side. It is notified that division of the measurement zones of the internal surface of the backlight module is not limited to what is shown in FIG. 3. The transmittance spectrum refers to the transmittance in response to each wavelength in a visible light band in this embodiment. Moreover, chromatic values of the plurality of measurement zones shown on the internal surface of the backlight module without the phosphor-based optical film are measured and collected by an optical measurement device (such as a spectra-radiometer and a color analyzer). A chromatic matrix is formed on the plurality of measurement zones shown on the internal surface of the backlight module. The chromatic matrix comprises the chromatic value of each of the plurality of measurement zones. The difference of the chromatic values can be detected from the chromatic matrix. Whether the chromatic values are within the range of standard chroma or not can also be detected from the chromatic matrix. The range of standard chroma will be described in detail.

Step S2: Gain a chromatic value of each of the plurality of measurement zones after each of the plurality of measurement zones matches the phosphor-based optical film.

Step S3: Check the chromatic value of each of the plurality of measurement zones gained in Step S2 to be within the range of standard chroma. According to the present embodiment, the range of standard chroma refers to "standard chroma±tolerance of chroma" where, in reality, the backlight module comprises a variety of sizes so the range of standard chroma differs according to the size of the backlight module.

In Step S3, if the chromatic value of each of the plurality of measurement zones after each of the plurality of measurement zones matches the phosphor-based optical film is in the range of standard chroma, screening of the phosphor-based optical film used in the backlight module is successful, and the process of screening is finished. It is notified that, the chromatic value of each of the plurality of measurement zones on the internal surface of the backlight module is different from another, so producing parameters (such as elements, proportion, and density of phosphor) of the phosphor-based optical film are different for each of the plurality of measurement zones. Therefore, a zone with a screened phosphor-based optical film which corresponds to a measurement zone and is produced according to producing parameters comprises producing parameters different from another zone. Each zone corresponds to its individual measurement zone. If the chromatic value of each of the plurality of measurement zones matching the phosphor-based optical film is not within the range of standard chroma, match at least one measurement zone with a new phosphor-based optical film (the producing parameters of the new phosphor-based optical film are different from those of the older phosphor-based optical film matching the at least one measurement zone), and return to Step S2.

S2 further comprises following steps:

Step S21: Gain a transmittance spectrum of the phosphor-based optical film matching each of the measurement zones.

Step S22: Multiply the transmittance in response to each wavelength of the transmittance spectrum of each of the plurality of measurement zones by the transmittance in response to each wavelength of the transmittance spectrum of the phosphor-based optical film, and then gain the transmittance spectrum of each of the plurality of measurement zones after each of the plurality of measurement zones matches the phosphor-based optical film.

Step S23: Gain the chromatic value of each of the plurality of measurement zones after each of the plurality of measurement zones matches the phosphor-based optical film based on the transmittance spectrum of each of the plurality of measurement zones matching the phosphor-based optical film in Step S22. In Step S22, the transmittance in response to each wavelength of the transmittance spectrum of each of the plurality of measurement zones matching the phosphor-based optical film is multiplied by a vision function (i.e., a photopic vision value which a wavelength responds to in different states), and tristimulus values are gained by means of integrals in the visible light band. Further, the chromatic value of each of the plurality of measurement zones matching the phosphor-based optical film is gained according to the gained tristimulus values. The chromatic value in the present embodiment is defined by the CIE 1931 color space though the chromatic value is not limited in the present invention. For example, the chromatic value is defined by the CIE1976 color space, etc.

In addition, quantum dots (QDs) have characteristics of wide spectra of excitation, successive distribution, narrow and symmetrical spectra of emission, adjustable color, stable chemical reaction of light, and long life of fluorescence. Owing to these strengths, the phosphor-based optical film is preferably a QD film.

Embodiment 2

Figure 4:
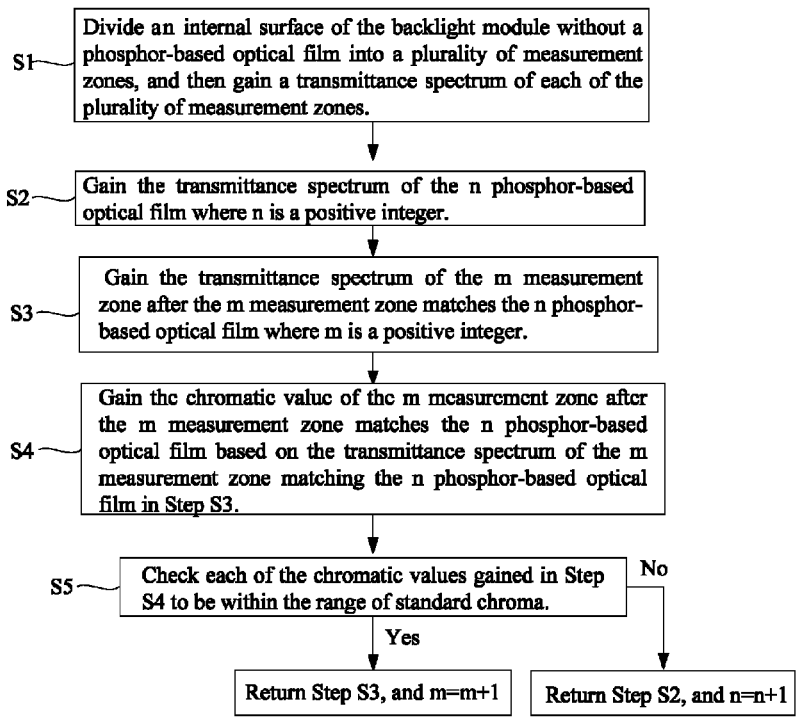
FIG. 4 is a flow chart showing a screening method of a phosphor-based optical film used in a backlight module according to a second embodiment of the present invention.

FIG. 4 is a flow chart showing a screening method of a phosphor-based optical film used in a backlight module according to a second embodiment of the present invention.

As shown in FIG. 4, the screening method of the phosphor-based optical film comprises following steps:

Step S1: Divide the internal surface of the backlight module without a phosphor-based optical film into a plurality of measurement zones, and then gain a transmittance spectrum of each of the plurality of measurement zones. The plurality of measurement zones can be distributed from one side of the backlight module to the farthest side in this step. For example, a first measurement zone A1, a second measurement zone A2, . . . , an m measurement zone Am are distributed in order from one side of the backlight module to the farthest side. It is notified that division of the measurement zones of the internal surface of the backlight module is not limited to what is shown in FIG. 3. The transmittance spectrum refers to the transmittance in response to each wavelength in a visible light band in this embodiment. Moreover, chromatic values of the plurality of measurement zones shown on the internal surface of the backlight module without a phosphor-based optical film are measured and collected by an optical measurement device (such as a spectra-radiometer and a color analyzer). A chromatic matrix is formed on the plurality of measurement zones shown on the internal surface of the backlight module. The chromatic matrix comprises the chromatic value of each of the plurality of measurement zones. The difference of the chromatic values can be detected from the chromatic matrix. Whether the chromatic values are within the range of standard chroma or not can also be detected from the chromatic matrix. The range of standard chroma will be described in detail.

Step S2: Gain the transmittance spectrum of the n phosphor-based optical film where n is a positive integer.

Step S3: Multiply the transmittance in response to each wavelength of the transmittance spectrum of the m measurement zone by the transmittance in response to each wavelength of the transmittance spectrum of the n phosphor-based optical film, and then gain the transmittance spectrum of the m measurement zone after the m measurement zone matches the n phosphor-based optical film where m is a positive integer.

S4: Gain the chromatic value of the m measurement zone after the m measurement zone matches the n phosphor-based optical film based on the transmittance spectrum of the m measurement zone matching the n phosphor-based optical film in Step S3. In Step S3, the transmittance in response to each wavelength of the transmittance spectrum of the m measurement zone matching the n phosphor-based optical film is multiplied by a vision function (i.e., a photopic vision value which a wavelength responds to in different states), and tristimulus values are gained by means of integrals in the visible light band. Further, the chromatic value of the m measurement zone matching the n phosphor-based optical film is gained according to the gained tristimulus values. The chromatic value in the present embodiment is defined by the CIE 1931 color space though the chromatic value is not limited in the present invention. For example, the chromatic value is defined by the CIE1976 color space, etc.

Step S5: Check each of the chromatic values gained in Step S4 to be within the range of standard chroma. According to the present embodiment, the range of standard chroma refers to "standard chroma±tolerance of chroma" where, in reality, the backlight module comprises a variety of sizes so the range of standard chroma differs according to the size of the backlight module.

In Step S5, if the chromatic value of the m measurement zone after the m measurement zone matches the n phosphor-based optical film is not in the range of standard chroma, return to Step S2 where n is set as n+1 (n=n+1). It is notified that, the chromatic value of every measurement zone on the internal surface of the backlight module is different from another, so producing parameters (such as elements, proportion, and density of phosphor) of the phosphor-based optical film are different for every measurement zone. Therefore, a zone which corresponds to a screened phosphor-based optical film and is produced according to producing parameters comprises producing parameters different from another zone. Each zone corresponds to its individual measurement zone. If the chromatic value of the m measurement zone after the m measurement zone matches the n phosphor-based optical film is within the range of standard chroma, return to Step S3 where m is set as m+1 (m=m+1).

In addition, QDs have characteristics of wide spectra of excitation, successive distribution, narrow and symmetrical spectra of emission, adjustable color, stable chemical reaction of light, and long life of fluorescence. Owing to these strengths, the phosphor-based optical film is preferably a QD film.

A backlight module 100 comprising a phosphor-based optical film 400 is provided in the present invention. The backlight module 100 is produced according to the screening method as described in the first or second embodiment. The detail of the backlight module 100 is shown in FIG. 5.

Figure 5:
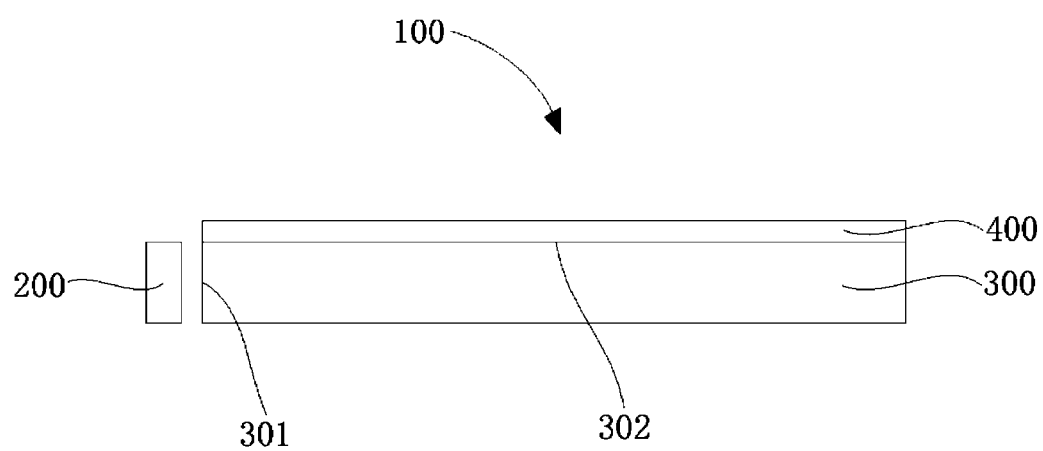
FIG. 5 shows a schematic diagram of the backlight of the present invention.

The backlight module 100 comprises a light source (such as a blue light-emitting diode) 200 and a light guide plate (LGP) 300 as shown in FIG. 5. The LGP 300 comprises a light input surface 301 and a light output surface 302. The light source 200 is disposed near the light input surface 301. The phosphor-based optical film 400 is screened according to the screening method as described in the first or second embodiment and disposed on the light output surface 302 by means of printing or spray coating.

In addition, QDs have characteristics of wide spectra of excitation, successive distribution, narrow spectra and symmetrical of emission, adjustable color, stable chemical reaction of light, and long life of fluorescence. Owing to these strengths, the phosphor-based optical film 400 is preferably a QD film.

The phosphor-based optical film 400 can be used as backlight of the backlight module 100, for the phosphor-based optical film 400 eventually converts the light produced by the light source 200 into white light. As described in the first or second embodiment, producing parameters of the phosphor-based optical film 400 vary with which part of the measurement zone (display zone) of the backlight module 100 matching the phosphor-based optical film 400. Different phosphor-based optical films 400 have different producing parameters. So the phosphor-based optical film 400 highly matches the backlight module 100. The backlight module 100 has higher saturation and penetration and better color uniformity.

Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A screening method of a phosphor-based optical film used in a backlight module, comprising steps of:
   Step a) dividing an internal surface of the backlight module without the phosphor-based optical film into a plurality of measurement zones, and gaining a transmittance spectrum of each of the plurality of measurement zones;
   Step b) gaining a chromatic value of each of the plurality of measurement zones after each of the plurality of measurement zones matches the phosphor-based optical film;
   Step c) checking the chromatic value of each of the plurality of measurement zones gained in Step b) to be within a range of standard chroma;
   the process of screening of the phosphor-based optical film used in the backlight module being finished if the chromatic value of each of the plurality of measurement zones matching the phosphor-based optical film is in the range of standard chroma;
   matching at least one measurement zone with a new phosphor-based optical film if the chromatic value of the at least one of the measurement zones matching the phosphor-based optical film is not within the range of standard chroma, and returning to Step b).

2. The screening method as claimed in claim 1, wherein Step b) further comprises steps of:
   Step b1) gaining the transmittance spectrum of the phosphor-based optical film matching each of the plurality of measurement zones;
   Step b2) gaining the transmittance spectrum of the phosphor-based optical film after each of the plurality of measurement zones matches the phosphor-based optical film;
   Step b3) gaining a chromatic value of each of the plurality of measurement zones after each of the plurality of measurement zones matches the phosphor-based optical film based on the transmittance spectrum gained in Step b2).

3. The screening method as claimed in claim 1, wherein the phosphor-based optical film matching each of the plurality of measurement zones comprises different producing parameters.

4. The screening method as claimed in claim 2, wherein the phosphor-based optical film matching each of the plurality of measurement zones comprises different producing parameters.

5. The screening method as claimed in claim 1, wherein the phosphor-based optical film is a quantum dot film.

6. The screening method as claimed in claim 2, wherein the phosphor-based optical film is a quantum dot film.

7. The screening method as claimed in claim 3, wherein the phosphor-based optical film is a quantum dot film.

8. The screening method as claimed in claim 4, wherein the phosphor-based optical film is a quantum dot film.

9. A screening method of a phosphor-based optical film used in a backlight module, comprising steps of:
   Step a) dividing an internal surface of the backlight module without the phosphor-based optical film into a plurality of measurement zones, and gaining a transmittance spectrum of each of the plurality of measurement zones;
   Step b) gaining the transmittance spectrum of an n phosphor-based optical film, and n being a positive integer;
   Step c) gaining the transmittance spectrum of an m measurement zone after the m measurement zone matches the n phosphor-based optical film, and m being a positive integer;
   Step d) gaining a chromatic value of the m measurement zone after each of the m measurement zone matches the n phosphor-based optical film based on the transmittance spectrum gained in Step c);
   Step e) checking the chromatic value of the m measurement zone after the m measurement zone matches the n phosphor-based optical film gained in Step d) to be within a range of standard chroma;
   if the chromatic value of the m measurement zone after the m measurement zone matches the n phosphor-based optical film is not in the range of standard chroma, returning to Step b) where n is set as n+1 (n=n+1);
   if the chromatic value of the m measurement zone after the m measurement zone matches the n phosphor-based optical film is within the range of standard chroma, returning to Step c) where m is set as m+1 (m=m+1).

10. The screening method as claimed in claim 9, wherein the phosphor-based optical film is a quantum dot film.

11. The screening method as claimed in claim 9, wherein each of the phosphor-based optical films comprises different producing parameters.

12. The screening method as claimed in claim 10, wherein each of the phosphor-based optical films comprises different producing parameters.

13. A backlight module, comprising a light source and a light guide plate (LGP), the LGP comprising a light input surface and a light output surface, and the light source being disposed near the light input surface wherein the backlight module further comprises a phosphor-based optical film which is screened according to the screening method as claimed in claim 1 or claim 9, and the phosphor-based optical film is disposed on the light output surface.

14. The backlight module as claimed in claim 13, wherein the phosphor-based optical film is a quantum dot film.

15. The backlight module as claimed in claim 13, wherein the phosphor-based optical film is disposed on the light output surface by means of printing or spray coating.

16. The backlight module as claimed in claim 14, wherein the phosphor-based optical film is disposed on the light output surface by means of printing or spray coating.

* * * * *